United States Patent [19]

Atkins

[11] 4,281,656

[45] Aug. 4, 1981

[54] HULKA-TYPE CLIP APPLICATOR

[75] Inventor: Colin A. Atkins, Englefield Green, England

[73] Assignee: Rocket of London Limited, Watford, England

[21] Appl. No.: 85,046

[22] Filed: Oct. 15, 1979

[30] Foreign Application Priority Data

Dec. 8, 1978 [GB] United Kingdom ............... 47669/78

[51] Int. Cl.³ ............................................. A61B 17/12
[52] U.S. Cl. .................................................. 128/325
[58] Field of Search ............... 128/326, 325, 346, 321, 128/334 R; 72/410; 29/243.56

[56] References Cited

U.S. PATENT DOCUMENTS 3,270,745  9/1966  Wood .............................. 128/346 X
4,169,476  8/1979  Hiltebrandt ..................... 128/346 X Primary Examiner—Robert W. Michell
Assistant Examiner—Michael H. Thaler
Attorney, Agent, or Firm—Prutzman, Kalb, Chilton & Alix

[57] ABSTRACT

A Hulka applicator has the forward end of the jaw-closing ram altered. The forward end has transversely-spaced jaw-engaging surfaces which engage the sides of the top of the upper clip jaw and cannot engage the clip spring.

10 Claims, 3 Drawing Figures

HULKA-TYPE CLIP APPLICATOR

BACKGROUND OF INVENTION

Recently there has been invented a surgical clip which is particularly adapted to occlude or produce necrosis in Fallopian tubes but which could have more general application to humans or to animals, and the clip is called a Hulka clip or a Hulka-type clip. There is a good descripton of the Hulka clip in U.S. Pat. No. 3,882,854, and of a modified Hulka-type clip in UK Patent Specification No. 1,513,650.

In general terms a Hulka-type clip has a pair of pivoted jaws for clamping tissue and a generally U-shaped spring which fits over the jaws and which can be slid forwards from a first position in which the ends of the spring hold the jaws open to a second position in which the ends of the spring (which are turned inwards) engage in recesses near the free ends of the jaw and lock the jaws closed. To guide the spring and prevent it slipping off sideways, it slides in shallow channels on the outside of each jaw, and a Hulka-type clip as referred to herein has such channels. The jaws are referred to as upper and lower jaws for convenience, but in practice the clip can be any side up, depending upon the way up the surgeon is holding the applicator.

Various applicators have been proposed for inserting the clip into the body and locking it over tissue, as described, for instance, in U.S. Pat. No. 3,882,854 or UK Patent Specification No. 1,486,351 - a more recent proposal is disclosed in U.S. Pat. No. 4,169,476. These applicators operate on the same basic principle, namely having a cradle for holding the lower jaw of the clip, a detent for preventing the clip falling out of the cradle and a first ram (which in an intermediate position may act as the detent) for riding along the top of the clip and closing the clip. When the jaw is fully closed, the first ram has passed beyond the locked position of the spring and engages the very front end of the jaw, closing the clip. In practice, the distal end of the first ram engages in the top channel of the clip to prevent the clip falling out of the cradle. There is also a second ram for engaging the rear end of the spring and pushing it forwards into its locking position once the clip has been closed over the tissue by the first ram.

In the case of U.S. Pat. No. 4,169,476 and UK Patent Specification No. 1,486,351, if the first ram has been fully advanced, it will not engage the spring as the spring is pushed forwards by the second ram and trouble-free operation can be expected.

On some occasions, in the use of the applicator of UK Patent Specification No. 1,486,351, there has been high resistance to the forward movement of the spring and hence of the second ram, and the spring has been distorted, leading to a risk that the clip may not be held perfectly closed or may even fall off. The reasons are not certain, but it is believed that on some occasions the surgeon may have allowed the first ram to retract slightly before actuating the second ram; the first ram would then bear on the top of the spring and apply a strong frictional resistance to its forward movement. Another possibility is that the tissue engaged by the jaws may have been too thick, so that the surgeon was unable to push the first ram right forward, with the same effect.

THE INVENTION

The invention provides an applicator of the type described wherein the forward end of the first ram is provided with a transversely-spaced jaw-engaging surfaces so that it engages the lateral portions of the top of the upper jaw and cannot engage the spring of the clip.

Using the applicator of the invention, the spaced jaw-engaging surfaces prevent the first ram engaging the spring even if the first ram is not fully forwards, and thus can reduce the risk of a spring being distorted. The first ram need not be so long as to be able to reach the very free end portion of the upper jaw.

There is one subsidiary problem with the applicator of UK Patent Specification No. 1,486,351. When the first ram is in its intermediate position (and its retraction is prevented by a safety catch), its very distal end acts as the detent to prevent the clip falling out of the cradle. The distal end cannot be further forward than the pivot of the clip as the clip must be open when the first ram is in its intermediate position, but the rear end of the clip is not very far behind the pivot. If the surgeon accidentally releases the safety catch and allows the first ram to retract by even as little as 0.25 or 0.4 mm., the clip can be released and fall out, e.g. into the abdominal cavity. The feature of forwardly projecting side pieces on the ram as provided by the present invention can avoid or reduce this problem in that although the jaw-engaging surfaces must be behind the pivot of the clip when the first ram is in its intermediate position, the foremost portions of the side pieces can project forwards beyond the pivot and help retain the clip in position.

DESCRIPTION OF THE PREFERRED EMBODIMENT

The invention will be further described, by way of example, by reference to the accompanying drawing, in which.

Figure 1:
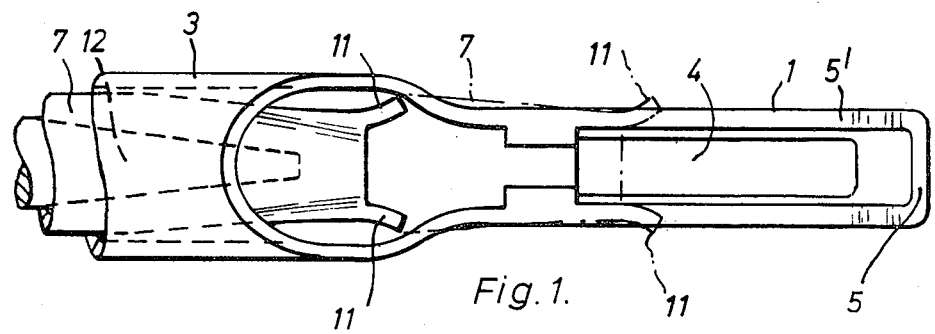
FIG. 1 is a top view of the distal end of a Hulka-type clip applicator with the first and second rams in the fully-retracted positions and no clip in position.

The clip is not described in detail, and can be exactly as described in U.S. Pat. No. 3,882,854, or in UK Patent Specification No. 1,513,650: the clip described in UK Patent Specification No. 1,513,650 has a modified rear end which, however, does not concern the present invention.

The applicator has a cradle 1 for holding the lower jaw 2 of the clip, the cradle 1 being a continuation of an outer tube 3 of the applicator. The cradle has a fenestration 4 and a U-shaped front wall 5 providing returns 5' on either side. The fenestration 4 is arranged that it will underlie the whole length of the clip spring 6 when the spring 6 is in its locked position, and thus contribute to preventing jamming of the spring 6 as it is pushed forward.

Figure 3:
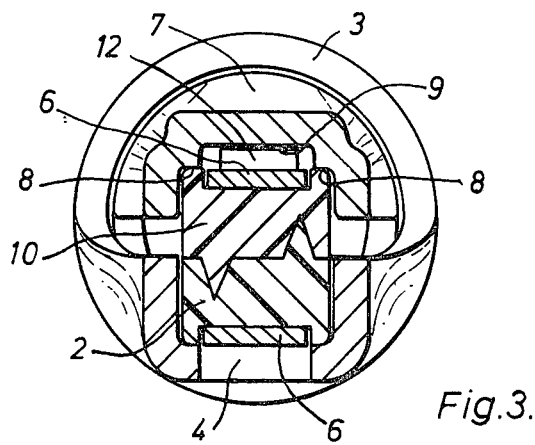
FIG. 3 is a cross-section along the line III—III in FIG. 2, a clip also being shown.

Within the outer tube 3 there is an inner tube or first ram 7 whose forward end is of generally U-section (see FIG. 3) and provides two transversely-spaced jaw-engaging surfaces 8 separated by a shallow groove 9 which is slightly wider than the spring 6; in this way, the jaw-engaging surfaces 8 cannot foul the spring 6.

Figure 2:
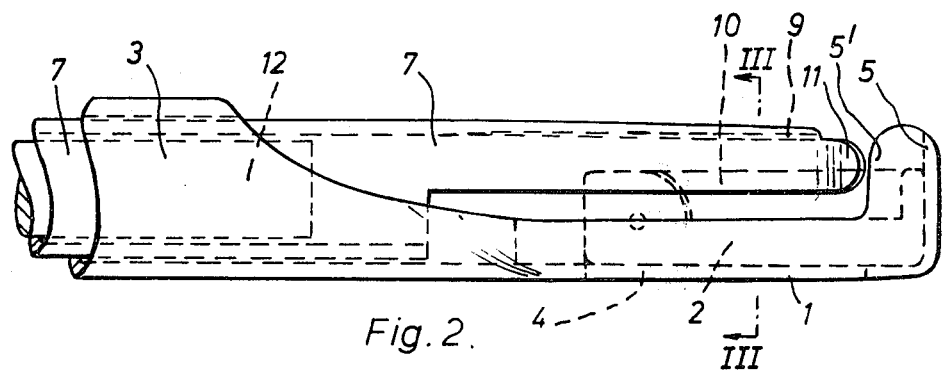
FIG. 2 is a side view of the distal end of the applicator, with the first ram in its fully advanced position, the second ram in its retracted position and the clip shown in faint lines.

When the first ram 7 is advanced, the jaw-engaging surfaces 8 ride along the lateral portions of the top of the clip upper jaw 10 and close the clip. The first ram 7 provides side pieces which pass down on either side of the upper jaw 10 of the clip, and the foremost portions 11 of the side pieces project forward beyond the jaw-engaging surfaces 8 and are outwardly flared. The clips have a manufacturing tolerance on width, as do the cradles 1; the cradle 1 is very shallow and a clip can be inclined 10° or 15° from its correct position (as seen looking at FIG. 3). The flared portions 11 will cam the clip into its correct position and ensure that it does not foul the first ram 7. The flared portions 11 are dimensioned so as to stop a bit short of the returns 5' of the front wall 5 (see FIG. 2), and the forward motion of the first ram 7 is limited for instance by a stop on the handle (not shown) of the applicator or by the first ram 7 engaging the outer tube 3, e.g. by engagement of the sides of the distal end of the first ram 7 with the narrowing down of the outer tube 3 to form the cradle 1. The small gap between the flared portions 11 and the returns 5' avoid any danger of piercing the mesosalpinx and perhaps damaging some of the tiny blood capillaries linked to the Fallopian tube artery.

In operation, the clip is put in the cradle 1 and the first ram 7 is advanced to its intermediate position indicated in dot-dash lines in FIG. 1, where it acts as a detent to prevent the clip falling out of the cradle 1. The distal end of the applicator and the clip are then inserted into the body, and when the clip is in its correct position, the first ram 7 is fully advanced to close the clip over the appropriate tissue; in theory, the first ram 7 need only pass just beyond the first point of the upper jaw 10, but for safety a greater movement of the first ram 7 is provided for; the second ram 12 is then advanced to engage the rear end of the spring 6 and push it forwards into its locking position. It will be seen that even if the first ram 7 is slightly retracted during this motion, the first ram 7 will not contact the spring 6 and will not impede the forward movement of the spring 6. The ram 7 is designed so that the jaw-engaging surfaces 8 reach as far forward as the front end of the spring 6, but do not reach as far as the very front end of the upper jaw 10.

The first and second rams 7,12 are then retracted fully, the clip released from cradle 1 and the applicator removed from the body, leaving the clip in position locked over the tissue.

I claim:

1. In an applicator for inserting and locking a Hulka-type clip that comprises a pair of pivoted jaws, namely an upper jaw and a lower jaw, and a generally U-shaped spring which fits over the jaws and can be slid forwards from a first, "clip open" position to a second "clip locked" position, wherein the applicator comprises:

a cradle for holding the lower jaw of the clip;
   a detent for preventing the clip falling out of the cradle;
   a first ram for riding along the top of the upper jaw of the clip and closing the clip, and
   a second ram for engaging the rear end of the spring of the clip and pushing it forward into its locking position once the clip have been closed by the first ram, the improvement wherein the forward end of said first ram is provided with transversely-spaced jaw-engaging surfaces that engage spaced lateral portions of the top of the upper jaw, said first ram being free from engagement with the spring of the clip during the closing and locking of the clip.

2. The applicator of claim 1, wherein the jaw-engaging surfaces of the forward end of the first ram are separated by a shallow groove.

3. The applicator of claim 2, wherein the forward end of the first ram has side pieces which pass down either side of the upper jaw of the clip, the foremost portions of the side pieces projecting forwards beyond the jaw-engaging surfaces.

4. The applicator of claim 2, wherein the jaw-engaging surfaces do not engage the very front portion of the upper jaw when the first ram is in its fully advanced position.

5. The applicator of claim 1, wherein the forward end of the first ram has side pieces which pass down either side of the upper jaw of the clip, the foremost portion of each side piece being outwardly flared.

6. The applicator of claim 5, wherein the jaw-engaging surfaces do not engage the very front portion of the upper jaw when the first ram is in its fully advanced position.

7. The applicator of claim 1, wherein the forward end of the first ram has side pieces which pass down either side of the upper jaw of the clip, the foremost portions of the side pieces projecting forwards beyond the jaw-engaging surfaces.

8. The applicator of claim 1, wherein the jaw-engaging surfaces do not engage the very front portion of the upper jaw when the first ram is in its fully advanced position.

9. The applicator of claim 1, wherein the forward end of the first ram has side pieces which pass down either side of the upper jaw of the clip, the foremost portion of each side piece being outwardly flared and projecting forwards beyond the jaw-engaging surfaces.

10. The applicator of claim 9, wherein the jaw-engaging surfaces do not engage the very front portion of the upper jaw when the first ram is in its fully advanced position.

* * * * *